(12) United States Patent
Salvermoser et al.

(10) Patent No.: US 11,504,168 B2
(45) Date of Patent: Nov. 22, 2022

(54) BONE FASTENER ASSEMBLY INSTRUMENT

(71) Applicant: Paradigm Spine, LLC, New York, NY (US)

(72) Inventors: Markus Salvermoser, Tuttlingen-Möhringen (DE); Stephan Eckhof, Rietheim-Weilheim (DE)

(73) Assignee: PARADIGM SPINE, LLC, New York, NY (US)

( * ) Notice: Subject to any disclaimer, the term of this patent is extended or adjusted under 35 U.S.C. 154(b) by 0 days.

(21) Appl. No.: 17/126,809

(22) Filed: Dec. 18, 2020

(65) Prior Publication Data

US 2021/0186584 A1 Jun. 24, 2021

Related U.S. Application Data

(60) Provisional application No. 62/951,018, filed on Dec. 20, 2019.

(51) Int. Cl.
| | | |
|---|---|---|
| *A61B 17/70* | (2006.01) | |
| *A61B 17/88* | (2006.01) | |
| *A61B 17/86* | (2006.01) | |
| *A61B 17/68* | (2006.01) | |

(52) U.S. Cl.
CPC ........ *A61B 17/7082* (2013.01); *A61B 17/683* (2013.01); *A61B 17/7062* (2013.01); *A61B 17/7074* (2013.01); *A61B 17/8665* (2013.01); *A61B 17/88* (2013.01); *A61B 17/8872* (2013.01); *A61B 17/8894* (2013.01); *A61B 17/7067* (2013.01)

(58) Field of Classification Search
CPC .............. A61B 17/683; A61B 17/7062; A61B 17/7067; A61B 17/7074; A61B 17/7076; A61B 17/7082; A61B 17/88; A61B 17/8872; A61B 17/8875
See application file for complete search history.

(56) References Cited

U.S. PATENT DOCUMENTS

| | | | | |
|---|---|---|---|---|
| 7,922,750 B2* | 4/2011 | Trautwein | .......... | A61B 17/7062 606/279 |
| 8,216,241 B2* | 7/2012 | Runco | ................ | A61B 17/7091 606/86 A |
| 8,439,953 B2* | 5/2013 | Mitchell | ............ | A61B 17/7068 606/279 |
| 9,173,695 B2* | 11/2015 | Salvermoser | ...... | A61B 17/7068 |

* cited by examiner

*Primary Examiner* — Larry E Waggle, Jr.
(74) *Attorney, Agent, or Firm* — Farber LLC

(57) ABSTRACT

A bone fastener assembly instrument that can assemble a two-component bone fastener during surgery is provided. The bone fastener may be of a type that comprises a threaded bolt and nut for securing an implantable device to bone, such as a spinous process. A method for using the bone fastener assembly instrument is also provided.

19 Claims, 12 Drawing Sheets

BONE FASTENER ASSEMBLY INSTRUMENT

CROSS-REFERENCE TO RELATED APPLICATIONS

This application claims the benefit of U.S. Provisional Application No. 62/951,018, filed on Dec. 20, 2019, the contents which are herein incorporated in their entirety by reference.

FIELD

The present disclosure relates to medical instruments for use during surgery, and more particularly to an instrument for assembling a fastener between an implantable device and bone.

BACKGROUND

Diseases of the spine cause significant morbidity. These diseases include abnormalities of the vertebrae, the intervertebral discs, the facet joints, and connective tissue around the spine. These abnormalities can be due to a number of causes, including mechanical injury or degenerative disc disease. Such abnormalities can cause instability to the spine, allowing the vertebral column to become misaligned and producing micromotion between adjacent vertebrae. Vertebral misalignment and micromotion may result in wear to the vertebral bony surfaces and ultimately cause severe pain. Further, these conditions are often chronic and progressive problems.

The treatments for spinal disorders can include long-term medical management or surgery. Medical management is generally directed at controlling the symptoms, such as pain, rather than correcting the underlying problem. For some patients, this may require chronic use of pain medications, which may alter patient mental state or cause other negative side effects.

Recently, a variety of interspinous stabilization devices have become available. These devices may be implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering spinal anatomy.

Currently available interspinous stabilization systems can be secured between adjacent spinous processes using a number of different mechanisms. For example, such devices can include sharp barbs or other surface projections that engage the bony surface of a spinous process. In addition, flexible ligaments or sutures can be placed around the implants and adjacent bone. However, it may be desirable to provide a more rigid and secure attachment to the spinous processes. For example, a rigid attachment may be desirable to prevent the interspinous device from migrating or slipping out of position. In addition, a rigid attachment may be desirable to limit movement and promote fusion at a selected vertebral level. Even further, it may be desirable to provide a device that can also fit interlaminarly between adjacent vertebrae, thereby enhancing the stability of the region.

Interlaminar-interspinous vertebral stabilization systems that can be easily implanted and can be securely attached to the spinous processes while being seated interlaminarly are disclosed in U.S. Pat. Nos. 7,922,750 and 10,398,478. These vertebral stabilization systems utilize a bone fastener to secure the implantable interlaminar-interspinous device to bone. The bone fastener comprises two separate, engageable components that are assembled together during the implantation process. An insertion tool, along with a tightening instrument, is provided for the assembly of the bone fastener.

It would be desirable to provide an improved insertion tool that can be used to assemble the bone fastener of these interlaminar-interspinous vertebral stabilization systems, as well as other systems, having a slim profile for ease of use and for use in minimally invasive surgeries (MIS). It would further be desirable to provide such an improved insertion tool enabling a shorter assembly time, while also being compatible with the same components and tools available with these systems.

SUMMARY

The present disclosure describes a bone fastener assembly instrument that can assemble a two-component bone fastener during surgery. The bone fastener may be of a type that comprises a threaded bolt and nut for securing an implantable device to bone, such as a spinous process. A method for using the bone fastener assembly instrument is also provided.

According to an aspect of the disclosure, the bone fastener assembly instrument can properly align the threaded screw and nut during assembly of the bone fastener through an aperture of an implantable device, thus allowing the bone fastener to secure the implantable device to bone. In one exemplary embodiment, an instrument for assembling a two-component bone fastener is provided. The instrument may comprise a pair of handles, each handle extending into an arm terminating in a working end configured to hold a component of the bone fastener. The instrument may also include a spring bias mechanism between the handles.

In addition, a transmission mechanism may be provided for rotating one of the components of the bone fastener. This transmission mechanism may comprise a drive shaft that operates through rotation of a series of worm gears or gear wheels. Rotation of the drive shaft can result in actuation of other parts such as screw holding components of the instrument. The drive shaft can be positioned between the handles and spring bias mechanism, thereby providing the instrument with an overall slim profile that allows for its use in minimally invasive surgeries (MIS).

In another exemplary embodiment, a collapsible insertion instrument for use with a two-component bone fastener is provided. The instrument may comprise a pair of handles, each handle extending into an arm terminating in a working end configured to hold one of the two components of the bone fastener. The instrument may also include a spring bias mechanism between the handles.

In addition, a transmission mechanism may be provided for rotating one of the two components of the bone fastener. This transmission mechanism may comprise a drive shaft that operates through rotation of a series of worm gears or gear wheels. Rotation of the drive shaft can result in actuation of other parts such as screw holding components of the instrument. The drive shaft can be positioned between the handles and spring bias mechanism, thereby providing the instrument with an overall slim profile that allows for its use in minimally invasive surgeries (MIS).

A catch and release mechanism for maintaining one of the arms in a retracted position during insertion, and an expanded position during assembly, may also be provided. This catch and release mechanism enables the bone fastener assembly instrument to maintain a low profile during use.

The two-component bone fastener may comprise a threaded bolt and a threaded nut. The exemplary instrument may be configured to rotate the threaded nut onto the threaded bolt.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

It is to be understood that both the foregoing general description and the following detailed description are exemplary and explanatory only, and are not restrictive of the disclosure, as claimed. Additional features of the disclosure will be set forth in part in the description which follows or may be learned by practice of the disclosure. The features of the disclosure will be realized and attained by means of the elements and combinations particularly pointed out in the appended claims.

DETAILED DESCRIPTION OF THE EMBODIMENTS

The present disclosure provides a bone fastener assembly instrument that can assemble a two-component bone fastener during surgery. The bone fastener may be of a type that comprises a threaded bolt and nut for securing an implantable device to bone, such as a spinous process. The bone fastener assembly instrument is configured to properly align the threaded screw and nut during assembly of the bone fastener through an aperture of an implantable device, thus allowing the bone fastener to secure the implantable device to bone. A method for using the bone fastener assembly instrument is also provided.

Figure 1A:
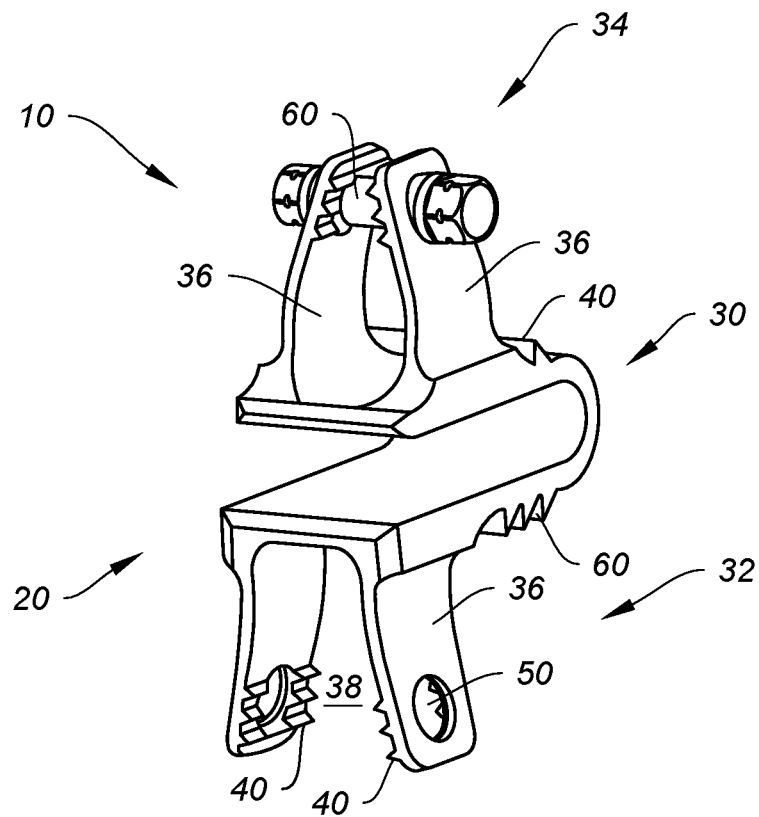
FIG. 1A is a perspective view of an exemplary embodiment of an interlaminar-interspinous vertebral stabilization system of the prior art.
Figure 1B:
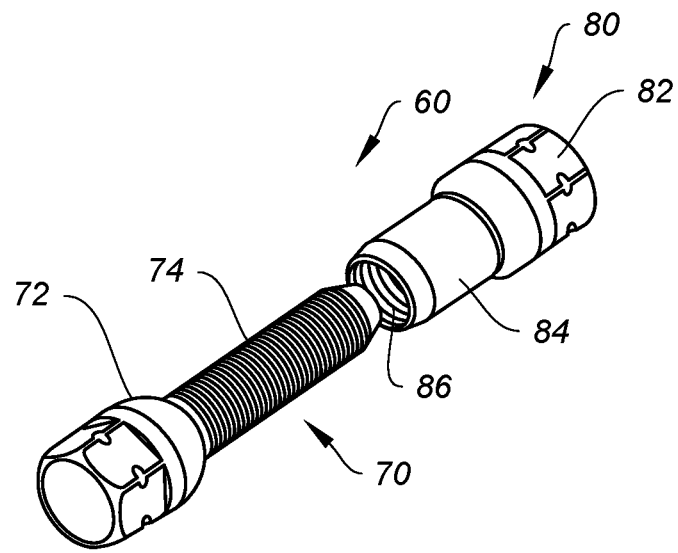
FIG. 1B is an enlarged exploded view of a bone fastener of the prior art usable with the interlaminar-interspinous vertebral stabilization system of FIG. 1A.
Figure 2:
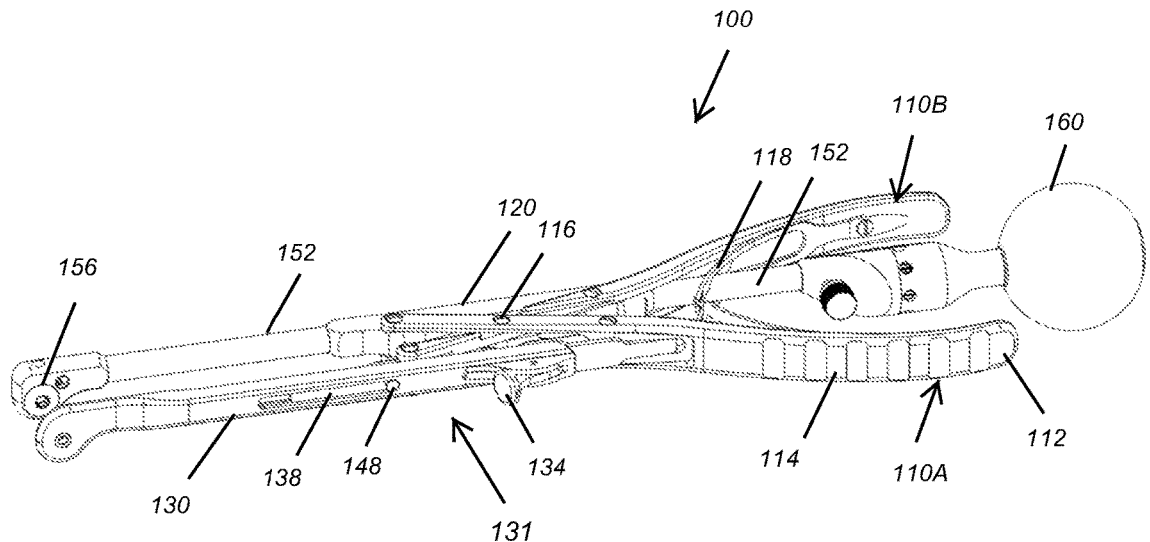
FIG. 2 is a perspective view of an exemplary embodiment of a bone fastener assembly instrument of the present disclosure, in an expanded configuration.

Turning now to the drawings, FIG. 1A shows an implantable interlaminar-interspinous vertebral stabilization system 10 for stabilizing adjacent vertebrae and FIG. 1B shows a bone fastener for use with the stabilization system 10, both of which are disclosed in U.S. Pat. No. 7,922,750. The prior art system 10 comprises an implantable device 20 configured for placement between the spinous processes of adjacent vertebrae. The system 10 can include one or more bone anchors 60 for securing the device 20 to spinous processes. Further, in one embodiment, the bone anchors 60 can rigidly fix the device 20 with respect to the spinous processes, thereby limiting movement at a selected vertebral level and promoting fusion at that level.

The device 20 may include a spacer body. The spacer body 20 may have various shapes and thicknesses, and can be produced from a variety of different materials. In one embodiment, the spacer body 20 may include a midsection 30 extending between an inferior section 32 and a superior section 34, as shown in FIG. 1A. When implanted in a patient, the superior section 34 is configured to contact a portion of a first spinous process, while the inferior section 32 is configured to contact a portion of a second, adjacent spinous process. In one embodiment, the midsection 30, inferior section 32, and superior section 34 may together form a substantially U-shaped spacer body 20, as shown. The spacer body 20 may be configured to be flexible and/or bendable, such as, for example, by providing an extendable and/or compressible midsection 30. The midsection 30 can act as a flexible hinge, allowing the superior section 34 and inferior section 32 to move away from or towards one another. Furthermore, the U-shaped spacer body enables the device 10 to be positioned, or fitted, interlaminarly after implantation, thereby enhancing the stabilization of the adjacent vertebrae.

To engage the spinous processes of adjacent vertebrae, the spacer body 20 may be provided with a pair of lateral walls or brackets 36 that extend from the inferior and superior sections 32, 34, as shown in FIG. 1A. Each of the pair of lateral walls 36 defines a stirrup 38 for receiving a spinous process. The spacer body 20 can be provided with lateral walls 36 of various sizes or heights to accommodate variations in patient anatomy. Likewise, the lateral walls 36 of different spacer bodies 20 may be provided at differing locations along the length of the inferior section 32 or superior section 34. The surgeon can thus select a suitably shaped and sized spacer body 20 depending on the particular vertebral level to be supported and the anatomy of the patient.

Further, the lateral walls 36 may also be adjustable with respect to the spacer body 20. For example, in one embodiment, the lateral walls 36 may be formed of a malleable material such that, after implantation, the surgeon may compress the lateral walls 36 together to reduce the gap between the lateral walls 36, thereby securely fixing the spacer body 20 to a spinous process located therein. In addition, the lateral walls 36 may be spread apart to facilitate insertion, as illustrated with the inferiorly located lateral wall 36 of FIG. 1A. The lateral walls 36 may be compressed or spread apart, for example, using surgical pliers or forceps.

The lateral walls or brackets 36 of the present invention can also include an aperture 50 for receiving a bone fastener to fix the brackets 36 to the spinous process. Such fastening members can ensure that the brackets 36 are pressed flat and/or securely against the spinous process in order to avoid any play of the brackets 36 with respect to the process. Further, the system 10 may act as a fusion-promoting device when the implantable device 20 is fastened to the spinous process in this manner.

As shown in FIG. 1B, the bone fastener 60 can be of a two-component type that includes a bolt 70 comprising a head 72 and a threaded, elongate body 74. To secure the bolt 70 within an aperture 50, a nut 80 is provided having a head 82, body portion 84, and threaded inner cavity 86 for receiving the threaded, elongate body 74 of the bolt 70. As the nut 80 is threaded onto the bolt 70, the lateral walls 36 may be drawn together. Thus, the bone fastener 60 and spacer body 20 may form a tight, secure connection with the spinous process. In some embodiments, the tight, secure connection between the body 20 and adjacent spinous processes will limit movement at the selected vertebral level, thereby promoting fusion at that level. In other embodiments, the nut 80 and bolt 70 may be tightened sufficiently to prevent the spacer body 20 from moving out of position between the spinous processes, but may be left sufficiently loose so as to allow a slight gap or clearance, to enable a small amount of play between the spacer body 20 and spinous processes, so as not to promote fusion, or cause fusion to occur more slowly. Further, in some embodiments, the system 10 can include two bone fasteners 60, so that both the inferior and superior lateral walls 36 can be securely fastened to spinous processes. Thus, it is contemplated that the device 20, when positioned between the spinous processes of two adjacent vertebrae, may be secured to one spinous process and not the other spinous process, or to both adjacent spinous processes.

FIGS. 2 to 7 illustrate an exemplary embodiment of a bone fastener assembly instrument 100 of the present disclosure. The instrument 100 may be useful for assembling the bone fastener 60 during implantation of the system 10. The bone fastener assembly instrument 100 allows the user the ability to secure the bone fastener 60 together, without crimping the wings 36 of the implantable device 10. FIGS. 8A to 8G illustrate a method of using the bone fastener assembly instrument 100 in this manner.

As shown, the bone fastener assembly instrument 100 may comprise a pair of handles 110A, 110B that extend into gripping portions 112. The gripping portions 112 may include a surface modification, such as for example, ridges, protrusions, bumps, or raised portions 114 to provide a secure gripping surface for the user. The handles 110A, 110B are connected to one another with a pivotable hinge 116 in a manner similar to scissors or pliers, much like the hinge described with the insertion tool of U.S. Pat. No. 7,922,750. A leaf spring 118 may be positioned between the handles 110A, 110B, as further shown.

Extending distally from the handles 110A, 110B are arms that include a holding portion at their free ends for holding one component of the two-component bone fastener 60. Handle 110A extends into first arm 120. The first arm 120 includes an actuation or transmission mechanism 150, as shown in greater detail in the partial cutaway view of FIG. 7.

Figure 7:
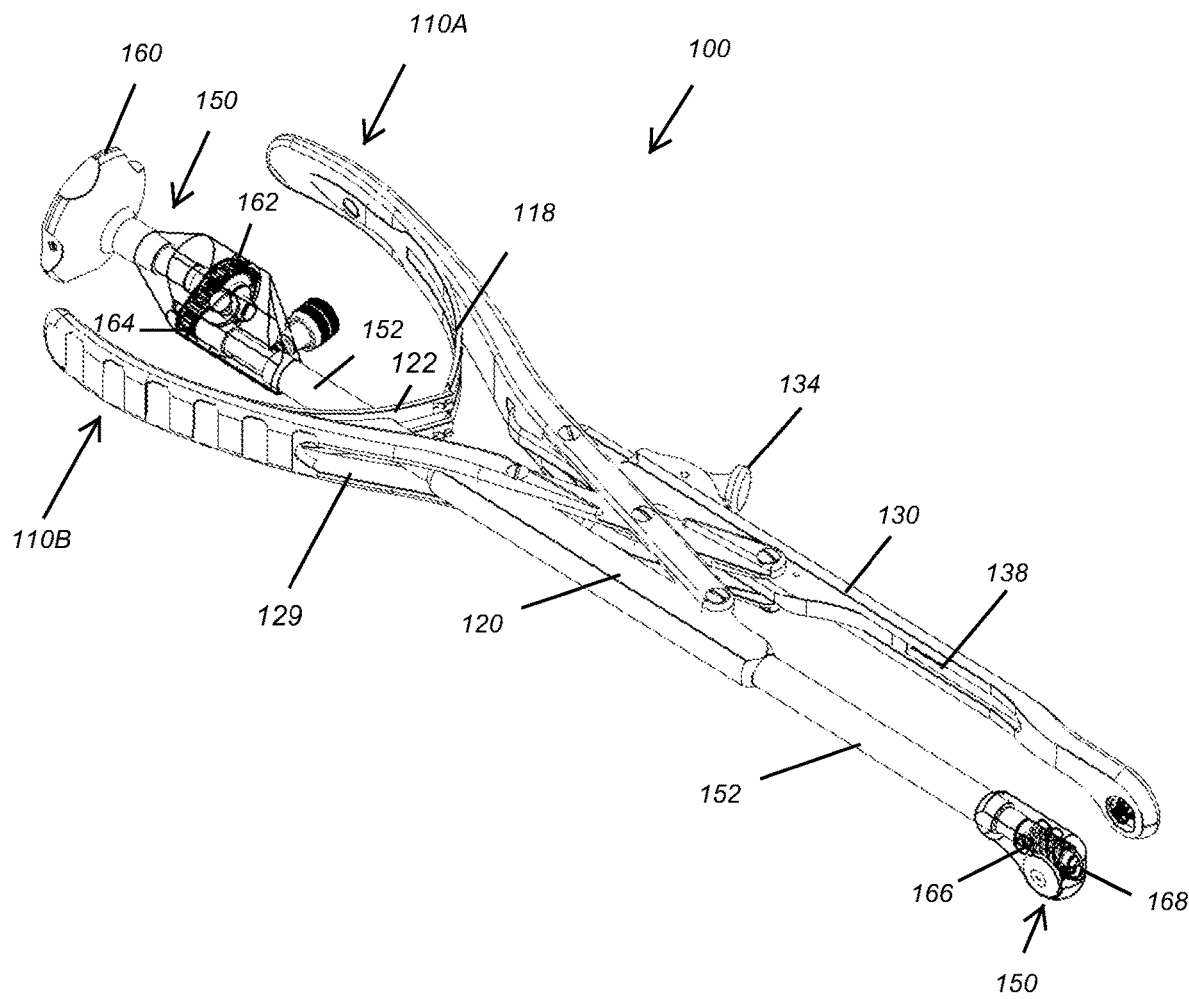
FIG. 7 is a partial cutaway view of the bone fastener assembly instrument of FIG. 2 showing a transmission mechanism comprising gear wheels.

The actuation or transmission mechanism 150 may include a drive shaft 152 that is configured to extend through the spring bias mechanism 118 at slot 122, and between the pair of handles 110A, 110B, as shown in FIG. 7. The drive shaft 152 extends into a rotatable knob 160. Rotation of the rotatable knob 160 causes internal gear wheels 162 to move the gear wheels 164 of the drive shaft 152 at its distal end, and consequently moves gear wheels 166 of the drive shaft 152 at its proximal end against gear wheels 168. This gear wheel 168 moves a first component holding portion 156 on the first arm 120 for holding one of the components of the bone fastener 60. The component may be either the threaded bolt 70, or the nut 80.

Figure 3:
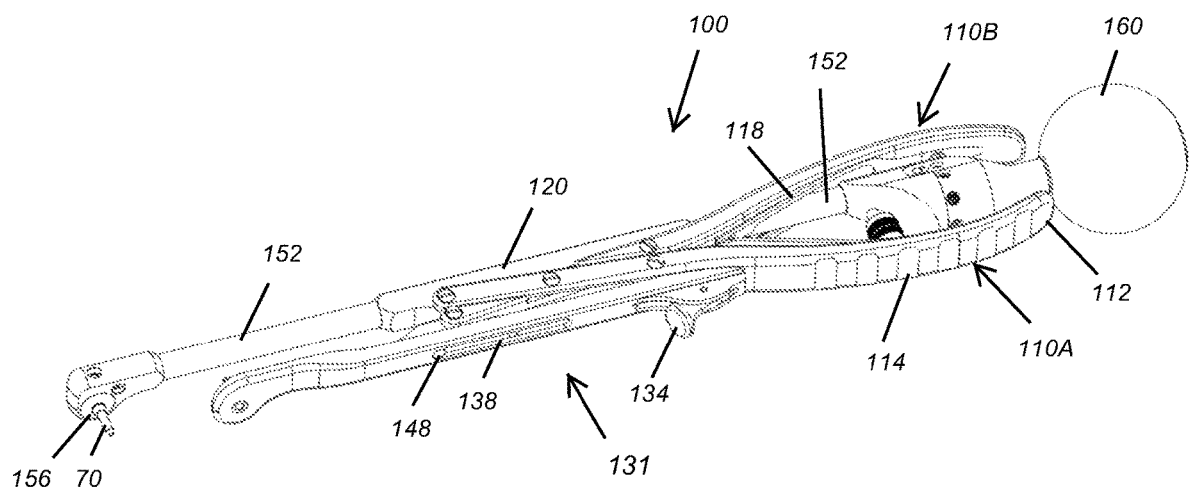
FIG. 3 is a perspective view of the bone fastener assembly instrument of FIG. 2, in a partially collapsed configuration and having a bone fastener and nut attached thereto.

As shown in FIG. 3, the first component holding portion 156 may be configured to hold onto the bolt 70. As shown in FIGS. 4, 5, 6A and 6B, the first component holding portion 156 may be configured to hold onto the nut 80. The ability of the holding portions 136, 156 of the arms 130, 120, respectively, to be able to hold either of the two components of the two-component fastener allows the user to select the orientation of the assembled fastener, i.e., the bolt 70 can be extending from the left or the right side.

Handle 110B may slidably connect to a second arm 130. The handle 110B has a hole 129 for the passage of the drive shaft 152 of the transmission mechanism 150. The second arm 130 may include a second component holding portion 136 for holding either the nut 80 or the threaded bolt 70 (see FIGS. 4, 5, 6A and 6B) of the bone fastener 60. Additionally, second arm 130 may also include a release button or finger rest 134 that serves to move the second arm 130, which may be configured to ratchet relative to handle 110B in a stepwise, lockable fashion. In one embodiment, as shown, this can be accomplished by providing the handle 110B with a notch 148 that can be held and/or slid within slot 138, allowing adjustment of the relative distance between the handle 110B and the working end of the second arm 130. The second arm 130 may be locked in position to help to keep the instrument 100 in a closed or collapsed configuration, such as in FIG. 3. In one embodiment, a catch-and-release mechanism 131 may be provided for this releasable locking of the second arm 130.

Figure 4:
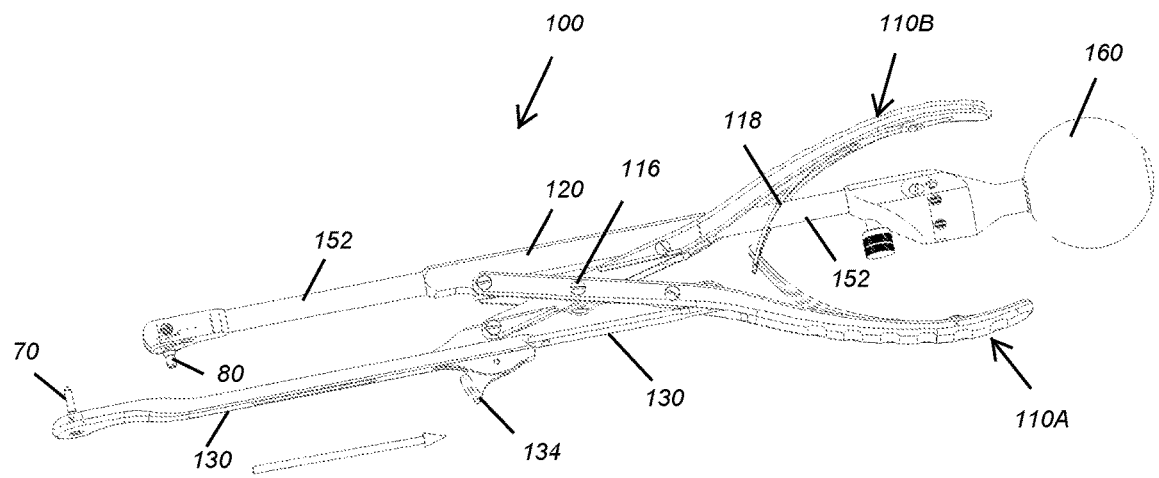
FIG. 4 is a perspective view of the bone fastener assembly instrument of FIG. 2, in a partially expanded configuration and having a bone fastener and nut attached thereto.
Figure 5:
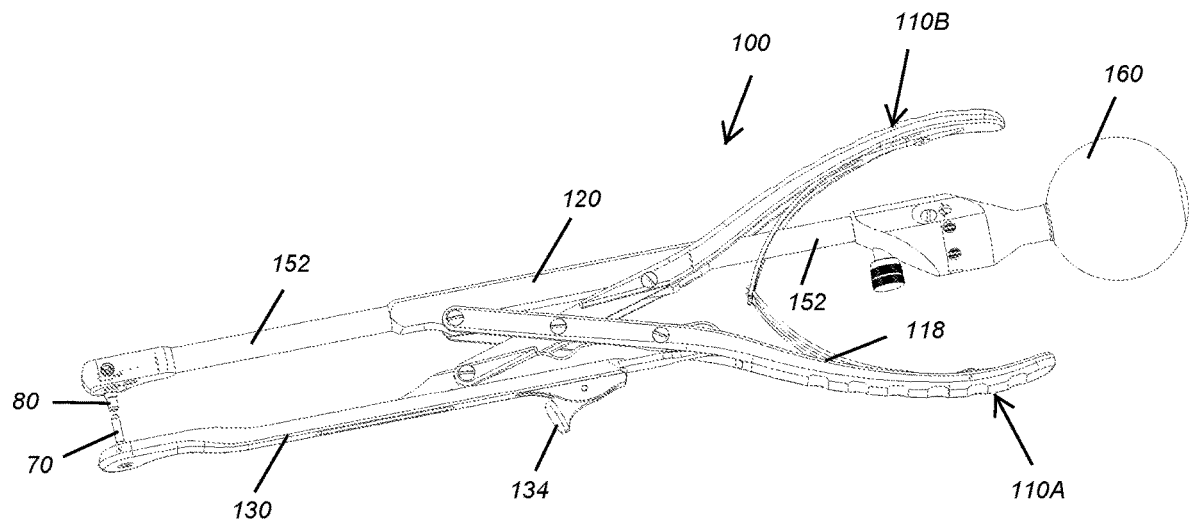
FIG. 5 is a perspective view of the bone fastener assembly instrument of FIG. 4, in a fully expanded configuration.
Figure 6A:
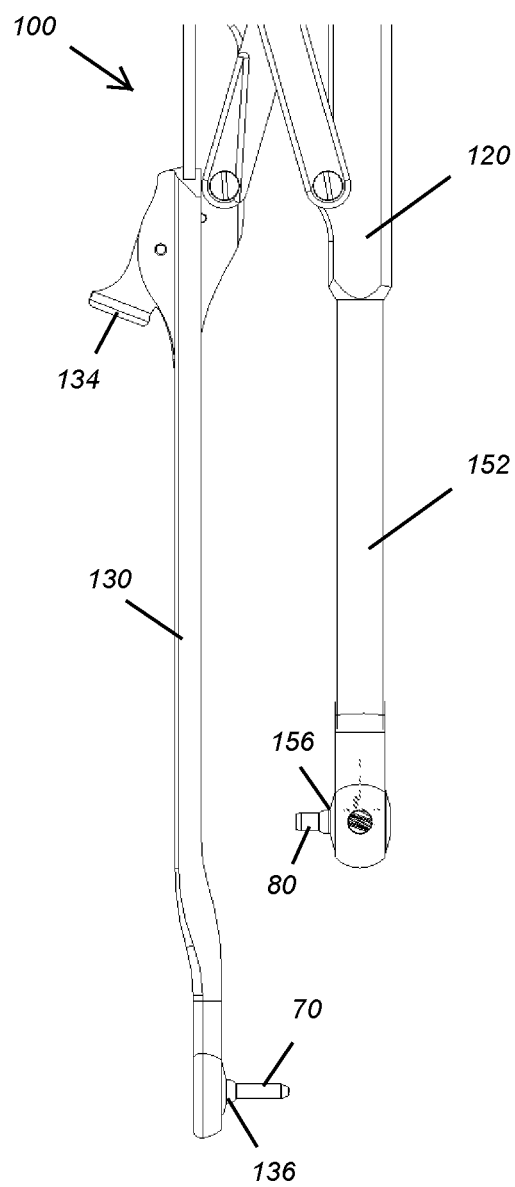
FIG. 6A is a partial top-down view of the bone fastener assembly instrument of FIG. 3.
Figure 6B:
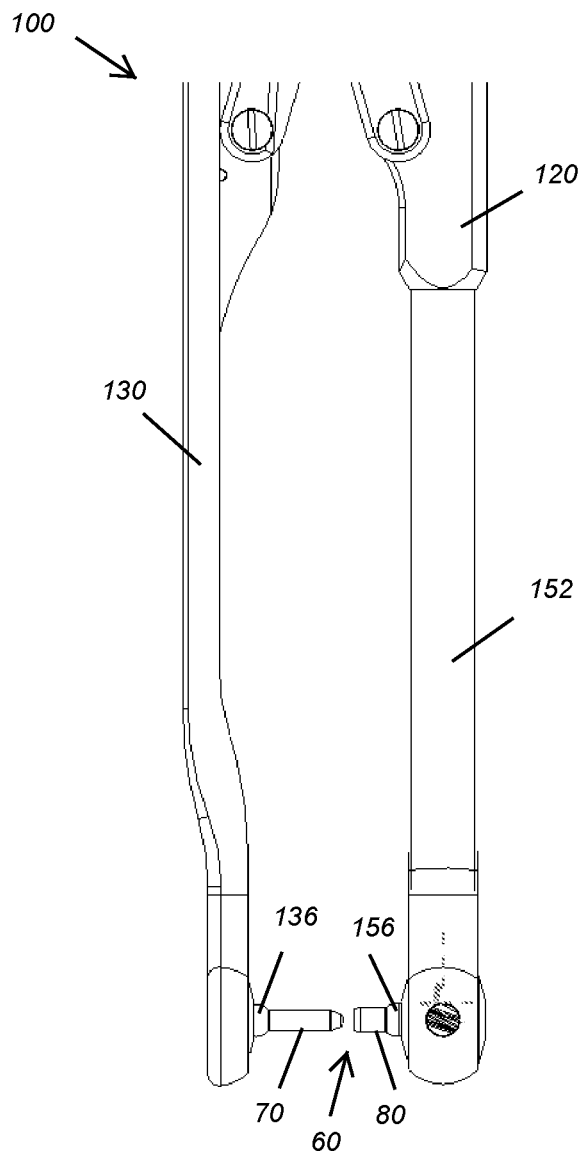
FIG. 6B is a partial top-down view of the bone fastener assembly instrument of FIG. 5.

The bone fastener assembly instrument 100 may be collapsible, and allow for a quicker, more streamlined approach to assembling a bone fastener, such as the two-component rivet of the prior art described herein. More importantly, the instrument 100 provides a space-saving solution to assembly of the bone fastener. FIGS. 2, 5, 6B and 7 show the instrument 100 in an open position, i.e., unlocked. FIGS. 3, 4 and 6A show the instrument 100 in a collapsed, or closed and locked position. In some embodiments, the width of the instrument 100 is in the range of about 15-25 mm, and preferably about 19 mm when in the closed position shown. In some embodiments, the instrument 100 may be easily disassembled and reassembled for cleaning and sterilization purposes.

FIG. 4 illustrates the manner in which the instrument 100 can be expanded, or opened. As shown by the arrow, the user may press against the finger rest or release button 134 to slidingly move down the instrument 100 and away from the handles 110A, 110B. In some embodiments, that sliding movement may comprise a ratcheting movement. When the second arm 130 is fully released or unlocked/open, the arms 120, 130 align, as shown in FIGS. 2, 5, 6B and 7. In some embodiments, the width of the instrument 100 in the open configuration is in the range of about 25-40 mm, and preferably about 32 mm.

FIGS. 8A-8G illustrate an exemplary method of using the bone fastener assembly instrument 100 of the present disclosure to assemble bone fastener 60 through the implantable interlamellar-interspinous device 20. First, the implantable device 20 is inserted between the spinous processes 2, 4 of adjacent vertebrae. Any appropriate surgical approach may be used to expose/visualize the spinous processes. After the implantable device 20 has been properly aligned so that the spinous processes are seated securely within the stirrups 38 of the device 20, a hole can be punched through the bones and through the apertures 50 of each of the pair of lateral walls 36, the apertures creating an easy path and serving as a guide for placement of the bone fastener 60 through this punched hole and through the spinous process. The holes may be formed using, for example, a hole puncher.

Figure 8A:
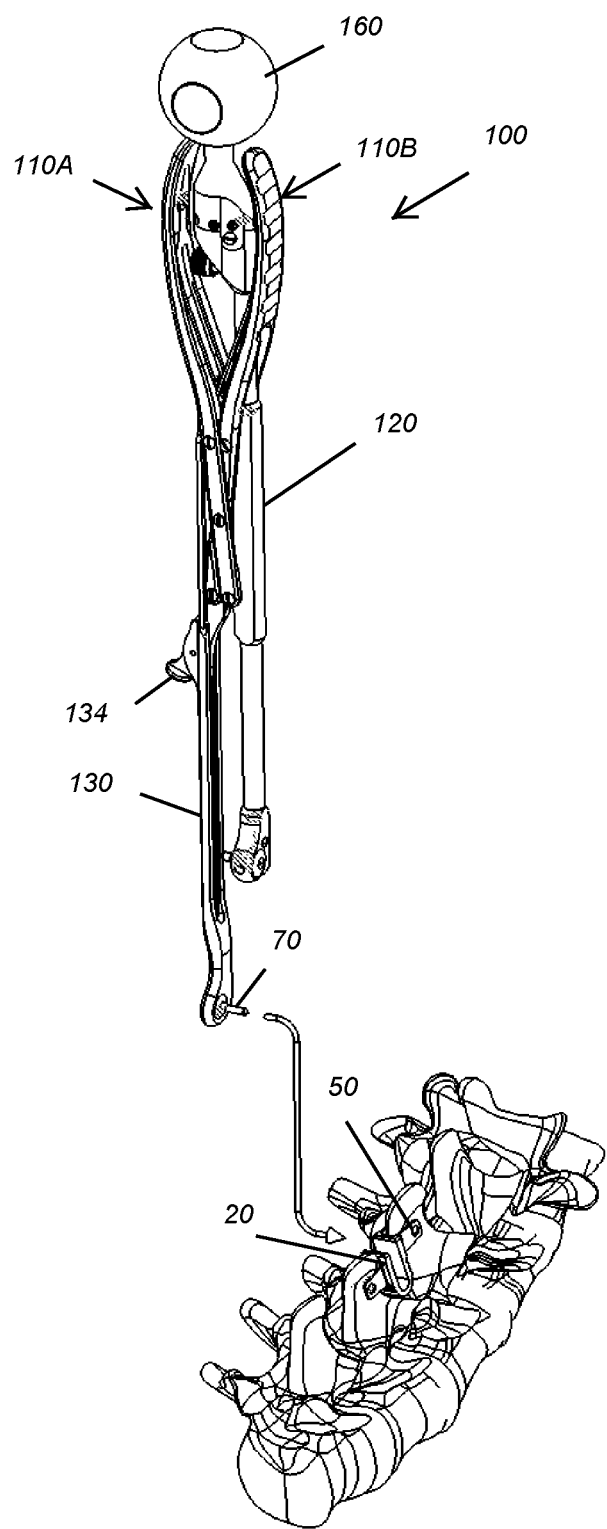
FIGS. 8A-8G illustrate an exemplary method of using the bone fastener assembly instrument of the present disclosure to assemble the bone fastener of FIG. 1B to the interlaminar-interspinous vertebral stabilization system of FIG. 1A.

As shown in FIG. 8A, the bone fastener 60 is loaded onto the instrument 100 in the expanded configuration, with the bolt 70 attached to the second component holding portion 136 of second arm 130, and the nut 80 attached to the first component holding portion 156 of the first arm 120.

Figure 8B:
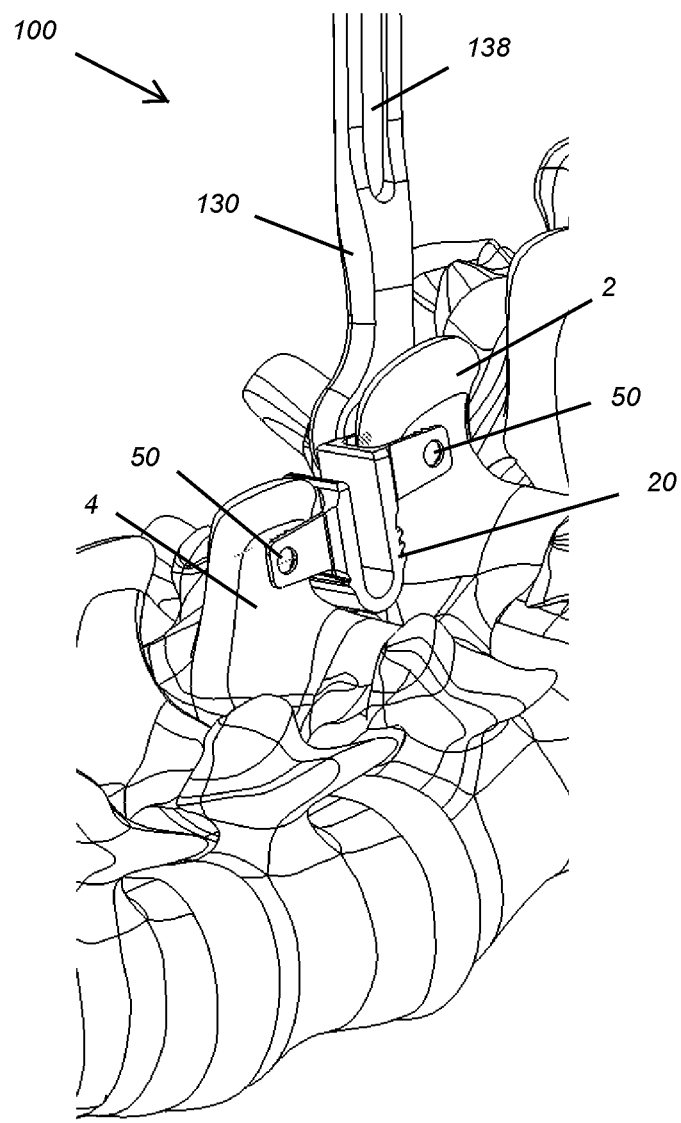

When the user is ready to assemble the bone fastener 60 together, the instrument 100 is first collapsed by depressing the release button 134, then the arm 130 may be slid away from the handle 110B and up to the end position, creating the slim profile configuration illustrated in FIG. 8A. In this collapsed configuration, the working ends of the arms as well as the handles are closed. With the bone fastener 60 loaded onto the instrument 100, the user introduces the bolt 70 toward the target site, which in this example is the aperture 50 of the implantable device 20. As indicated by the arrow in FIG. 8A, the user approaches the target site by aligning the attached bolt 70 to the target location. Thus, the instrument 100 allows a starting approach that only requires one arm to be aligned, and allows the ability to have the other arm positioned away from the active site to keep the area clear and allow maximum visibility and working space, as represented in FIG. 8B.

Figure 8C:
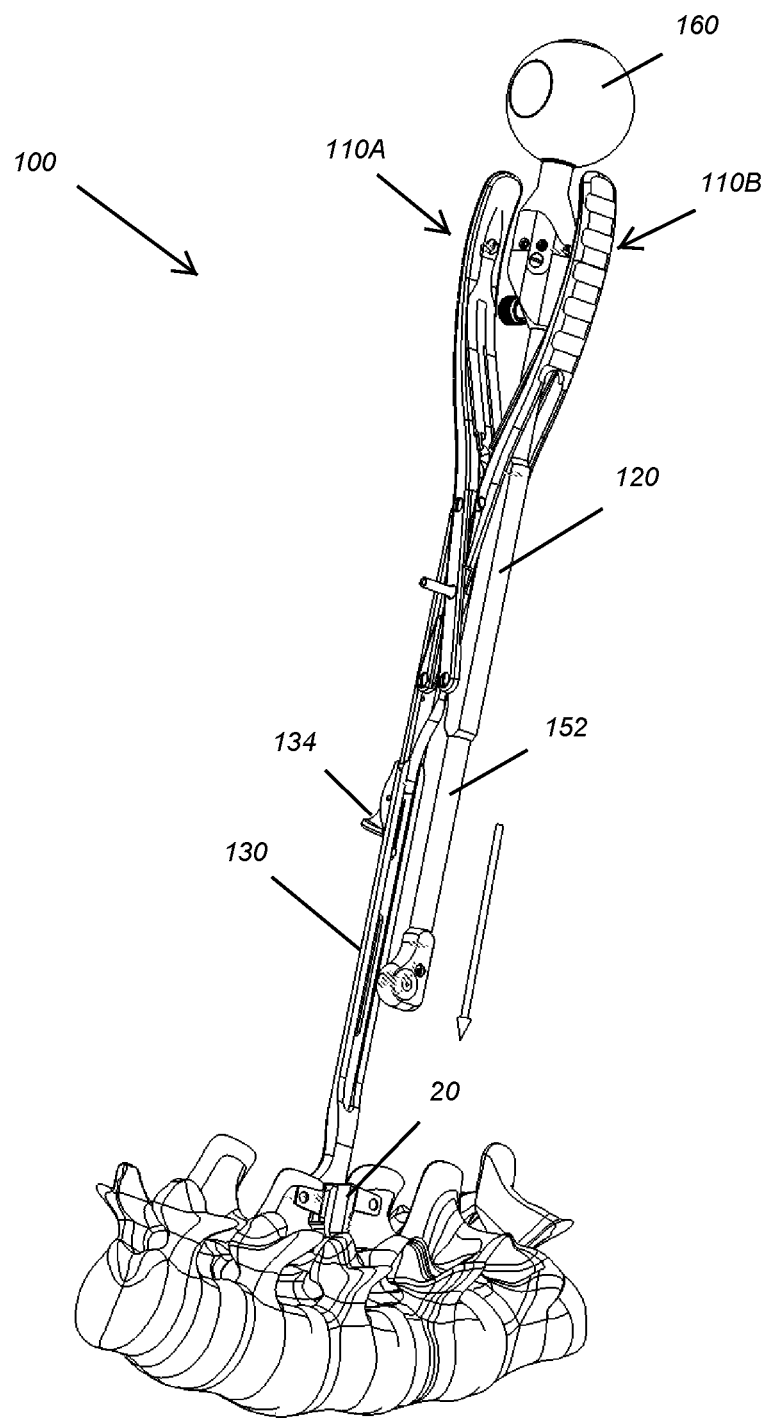
Figure 8D:
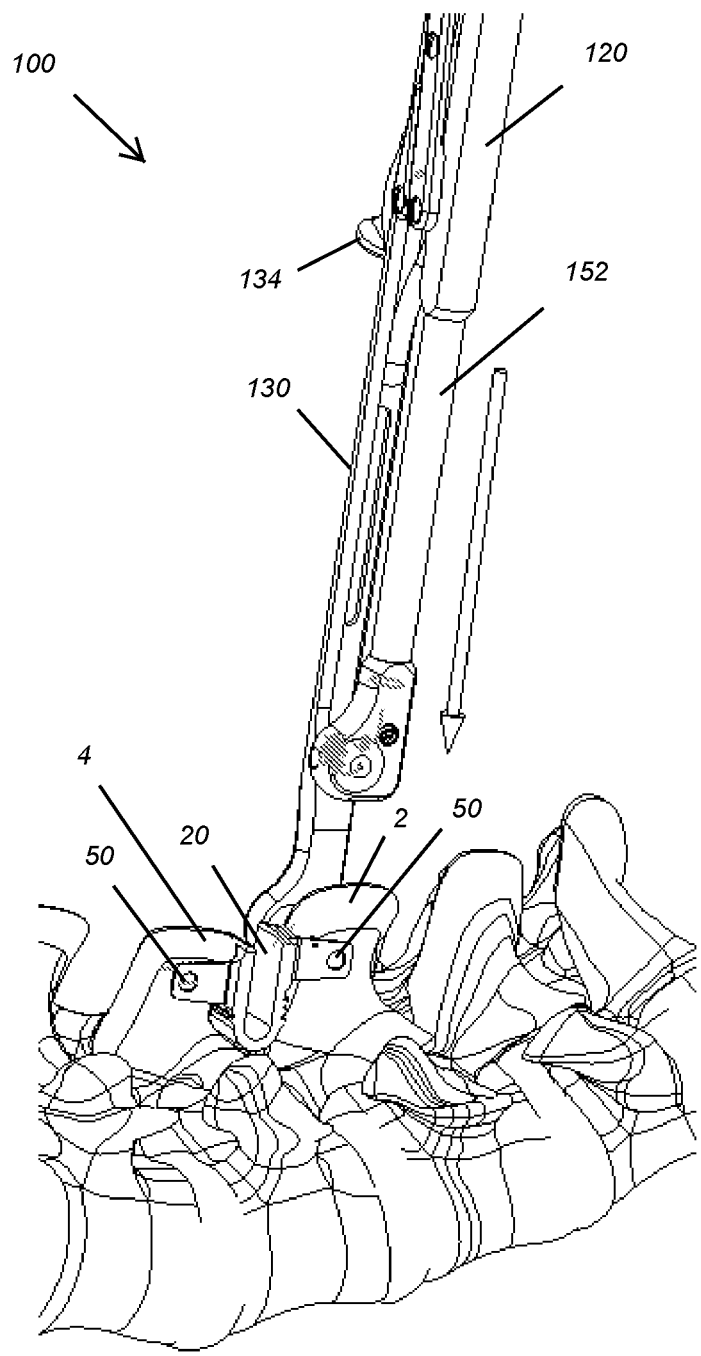
Figure 8E:
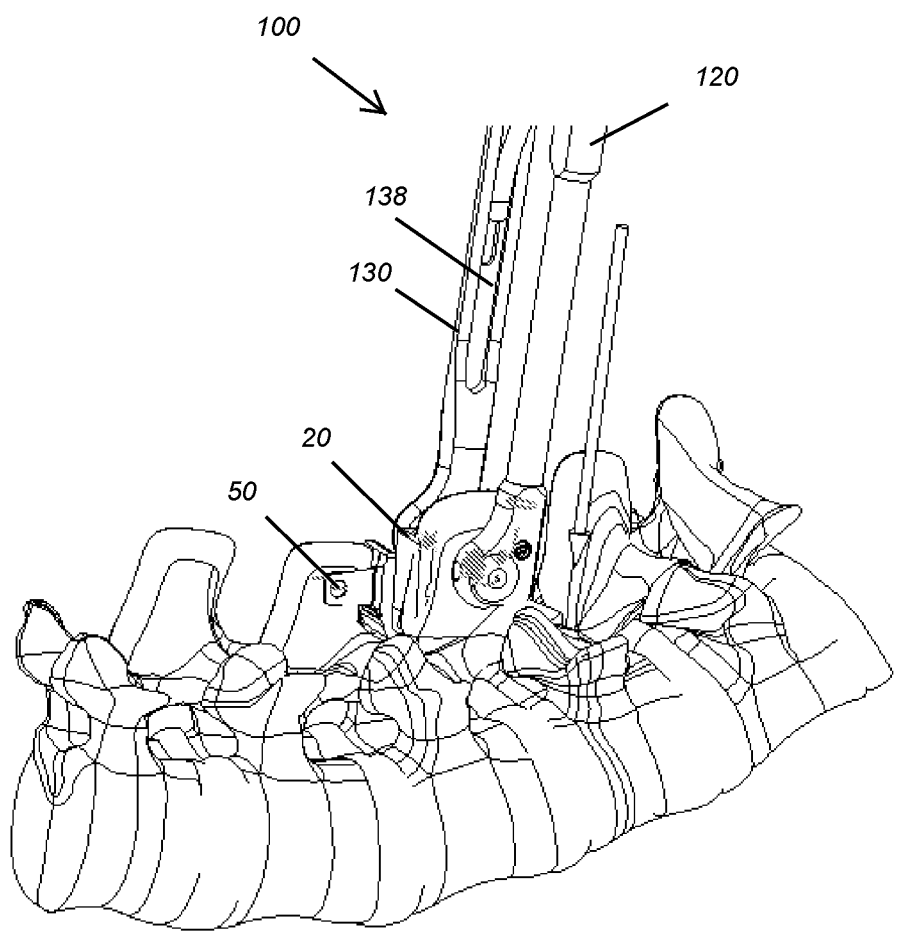
Figure 8F:
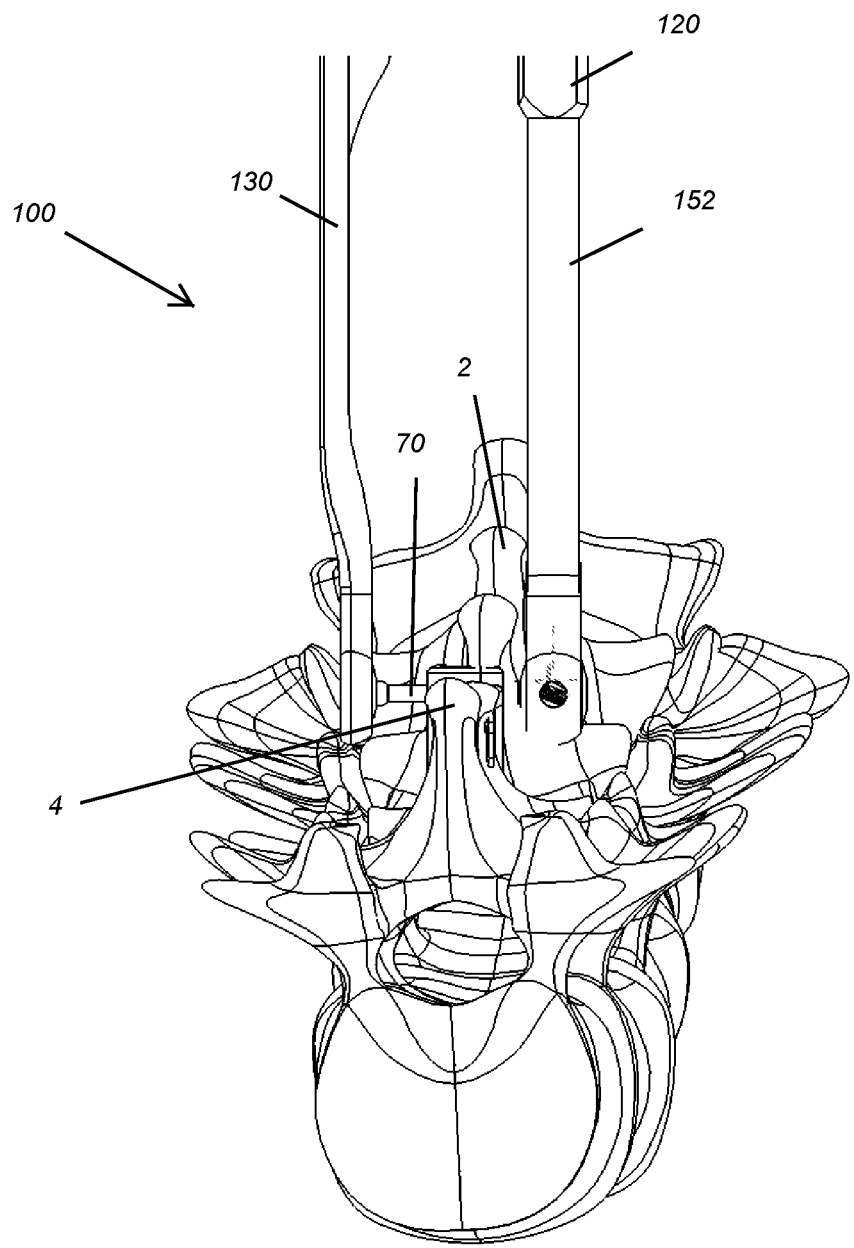

Once the second arm 130 holding the bolt 70 is in position, the instrument 100 is released or expanded by again depressing the release button to allow the rest of the instrument 100 to travel down relative to the second arm 130 and towards the target site, as shown in FIG. 8C. This position opens up the working ends of the arms 120, 130. As illustrated in FIGS. 8C, 8D and 8E, the instrument 100 can travel down relative to second arm 130 until the instrument 100 is fully expanded, thereby aligning the free ends of the arms 120, 130 and consequently the attached nut 80 with the attached bolt 70 on opposed sides of the implantable device 20, as shown in FIGS. 8E and 8F.

Figure 8G:
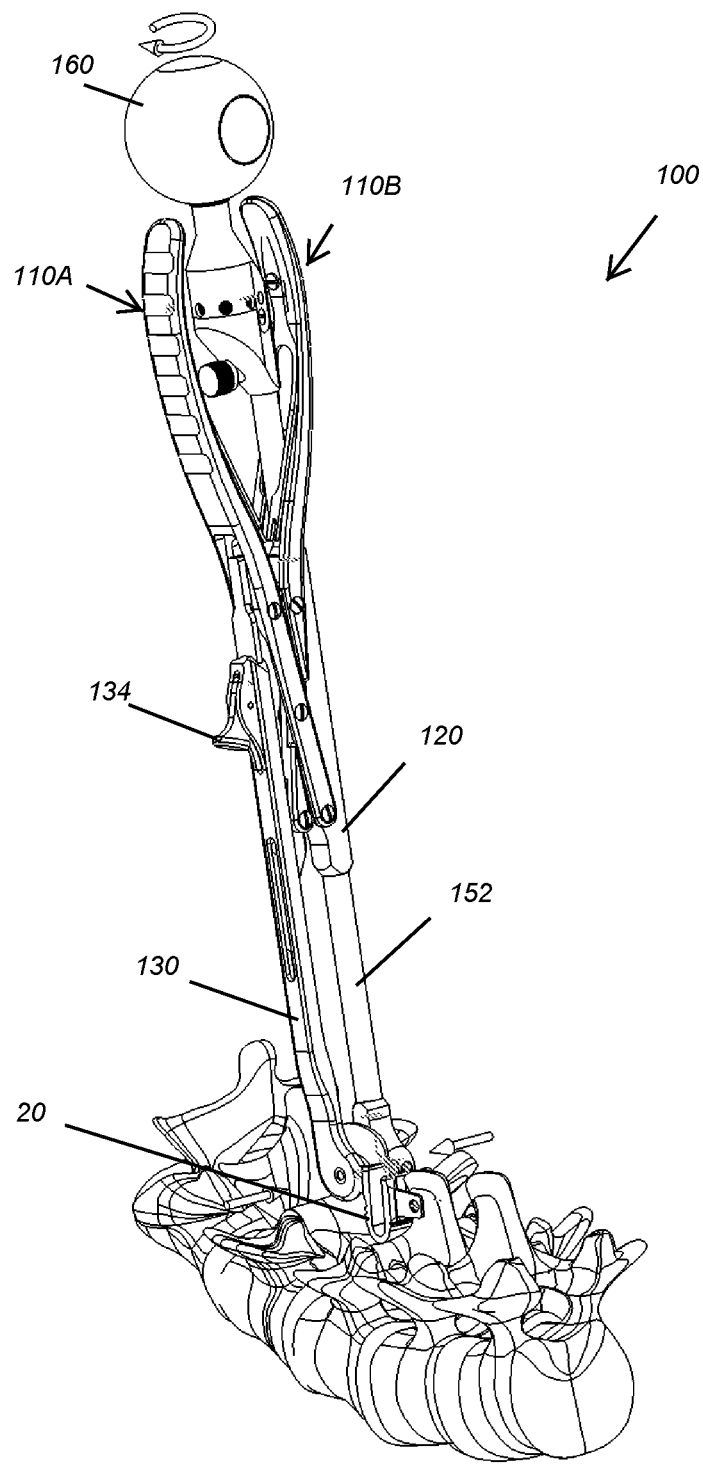

When it has been determined that the free ends of the arms are aligned and alignment of the bolt 70 and nut 80 is axially correct, the knob 160 can be turned, as shown in FIG. 8G. Turning the knob 160 causes the actuation of the transmission mechanism 150 and rotation of the nut 80, thereby causing the threading of the nut 80 onto the bolt 70.

The assembly instrument 100 facilitates alignment and threading of the bolt 70 and nut 80. For example, since there may be limited space available on lateral sides of the walls 36, it may be difficult for a surgeon to position the bolt 70 and nut 80 through a spinous process. The assembly instrument 100 maintains the bolt 70 and nut 80 in the properly aligned position so as to ensure that they easily thread together during assembly, while also providing a space-saving solution of allowing one arm to be extended and one arm to be retracted in the initial approach. Further, the assembly instrument allows for quick rotation of the nut 80 to secure the components to one another.

In addition, the assembly instrument 100 can maintain its slim profile at all times during either the expanded (open) or collapsed (closed) position by positioning the transmission mechanism 150, which includes drive shaft 152 and knob 160, within the handles 110A, 110B, as shown in FIGS. 8A and 8G.

In some embodiments, one or more additional instruments may be provided to assist in positioning the spinous processes of the vertebrae to be treated. For example, to properly implant the device 20 between spinous processes of the lumbar vertebrae, it may be desirable to position the patient in a certain degree of lordosis. However, during surgery, the patient may not be positioned ideally. Therefore, to assist the surgeon in producing the desired degree of lordosis, a pair of compression pliers may be provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An instrument for assembling a two-component bone fastener, comprising:
   a pair of handles, the pair of handles including a first handle extending into a first arm and a second handle extending into a second arm, each of the first arm and second arm terminating in a working end configured to hold a component of the bone fastener;
   a spring bias mechanism between the first handle and the second handle, the spring bias mechanism having a slot;
   a transmission mechanism connected to the first arm for rotating one of the components, the transmission mechanism extending through the slot in the spring bias mechanism and through a hole in the second handle; and
   a catch and release mechanism for maintaining one of the first arm and the second arm in a retracted position during insertion and an expanded position during assembly.

2. The instrument of claim 1, wherein the two-component bone fastener comprises a threaded bolt and threaded nut, and the working ends are configured to hold the threaded bolt and threaded nut in alignment.

3. The instrument of claim 1, wherein the spring bias mechanism comprises a leaf spring.

4. The instrument of claim 1, wherein the transmission mechanism comprises a drive shaft and a rotatable knob.

5. The instrument of claim 4, wherein the drive shaft comprises gear wheels.

6. The instrument of claim 5, wherein the gear wheels of the drive shaft cooperate with gear wheels of the rotatable knob and gear wheels of a component holding portion of the first arm.

7. The instrument of claim 1, wherein the catch and release mechanism comprises a ratcheting mechanism.

8. The instrument of claim 1, wherein the instrument can be fully disassembled.

9. The instrument of claim 1, wherein one of the first arm and second arm is slidable relative to one of the first handle and the second handle.

10. The instrument of claim 9, further including a finger rest for effecting the sliding of the arm.

11. The instrument of claim 9, wherein one of the arms includes a slot for sliding engagement of one of the handles.

12. The instrument of claim 11, wherein the sliding engagement is a lockable engagement.

13. The instrument of claim 1, wherein each of the working ends includes a bone fastener component holding portion.

14. The instrument of claim 13, wherein the bone fastener component holding portion is configured to hold either a threaded bolt or a nut.

15. The instrument of claim 1, wherein the handles are attached at a pivotable hinge.

16. A collapsible insertion instrument for use with a two-component bone fastener, comprising:
   a pair of handles, the pair of handles including a first handle extending into a first arm and a second handle extending into a second arm, each of the first arm and second arm terminating in a working end configured to hold one of the two components of the bone fastener;

a spring bias mechanism between the first handle and the second handle, the spring bias mechanism having a slot;
a transmission mechanism connected to the first arm for rotating one of the two components, the transmission mechanism extending between the pair of handles and the spring bias mechanism, the transmission mechanism extending through the slot in the spring bias mechanism and a hole in the second handle; and
a catch and release mechanism for maintaining one of the first arm and the second arm in a retracted position during insertion and an expanded position during assembly.

17. The instrument of claim 16, wherein the two-component bone fastener comprises a threaded bolt and a threaded nut.

18. The instrument of claim 17, further being configured to rotate the threaded nut onto the threaded bolt.

19. An instrument for assembling a two-component bone fastener, comprising:
a pair of handles, each handle extending into an arm terminating in a working end configured to hold a component of the bone fastener;
a spring bias mechanism between the handles;
a transmission mechanism connected to a first arm for rotating one of the components, the transmission mechanism extending between the pair of handles and the spring bias mechanism, the transmission mechanism comprising a drive shaft and a rotatable knob, the drive shaft comprising gear wheels that cooperate with the gear wheels of the rotatable knob and gear wheels of a component holding portion of the first arm; and
a catch and release mechanism for maintaining one of the arms in a retracted position during insertion and an expanded position during assembly.

\* \* \* \* \*